United States Patent [19]

Wallace et al.

[11] Patent Number: 5,165,415
[45] Date of Patent: Nov. 24, 1992

[54] SELF CONTAINED HAND HELD ULTRASONIC INSTRUMENT FOR OPHTHALMIC USE

[75] Inventors: David A. Wallace, Beverly Hills; Steven E. Feldon, San Marino, both of Calif.

[73] Assignee: Bio-Rad Laboratories, Inc., Cambridge, Mass.

[21] Appl. No.: 861,334

[22] Filed: Mar. 30, 1992

Related U.S. Application Data

[63] Continuation of Ser. No. 352,681, May 10, 1989, abandoned, which is a continuation of Ser. No. 267,746, Nov. 2, 1988, abandoned, which is a continuation of Ser. No. 145,643, Jan. 13, 1988, abandoned, which is a continuation of Ser. No. 781,148, Sep. 27, 1985, abandoned.

[51] Int. Cl.$^5$ .................................. A61B 8/10
[52] U.S. Cl. ..................... 128/661.06; 128/662.03
[58] Field of Search ................. 128/661.06, 662.03, 128/645–647, 652, 745; D24/10, 17, 18, 23

[56] References Cited

U.S. PATENT DOCUMENTS

| | | | |
|---|---|---|---|
| D. 205,182 | 7/1966 | Wiseman | D24/11 |
| D. 226,583 | 3/1973 | Welsh | D24/23 |
| 3,049,001 | 8/1962 | Mackay et al. | 128/645 |
| 3,656,481 | 4/1972 | Ness | 128/1.4 |
| 3,677,074 | 7/1972 | Murr | 128/645 |
| 4,127,114 | 11/1978 | Bretscher | 128/667 |
| 4,192,317 | 3/1980 | Munnerlyn et al. | 128/646 |
| 4,213,464 | 7/1980 | Katz et al. | 128/645 |
| 4,261,367 | 4/1981 | Freese | 128/661.06 |
| 4,413,629 | 11/1983 | Durley, III | 128/660 |
| 4,530,362 | 7/1985 | Hetz | 128/660 |
| 4,582,066 | 4/1986 | Barnes et al. | 128/661 |
| 4,583,553 | 4/1986 | Shah et al. | 128/708 |
| 4,637,403 | 1/1987 | Garcia et al. | 128/770 |

FOREIGN PATENT DOCUMENTS 3207255 9/1983 Fed. Rep. of Germany ...... 128/660

OTHER PUBLICATIONS

Storz, Brochure "Corneo-Scan Ultrasonic Pachymeter" 1981.
Giglio et al, "A Hand-Held Probe for Acoustic Coupling in Ultrasonic Intraocular Distance Measurements of Young Children", American Journal of Optometry, 1975 pp. 1025–1030.

*Primary Examiner*—Ruth S. Smith
*Attorney, Agent, or Firm*—Lyon & Lyon

[57] ABSTRACT

Disclosed is a completely portable, hand-held digital ultrasonic instrument about the size and shape of an ordinary pen. The housing is contoured such that it can be easily grasped in the manner of a writing pen. An activation button is located on the interior dorsal surface in close approximation to the index fingertip of the user. A liquid crystal display provides a digital readout of a thickness measurement on the barrel of the instrument housing. The instrument incorporates a 10 MHz or 20 MHz solid phase piezoelectric transducer, a microprocessor, a gate array, a hybrid analog circuit, a liquid crystal display, batteries and a removable battery cover. The 20 MHz transducer is used to measure corneal thickness and is attached to a swan neck connector which is attached to the instrument housing. The 10 MHz transducer is used for measuring axial length and it is attached to a truncated conical connector which is also attached to the instrument housing. In addition, a pinjack connector is available to link the unit to other electronic media such as a microcomputer, personal computer, or printer.

9 Claims, 2 Drawing Sheets

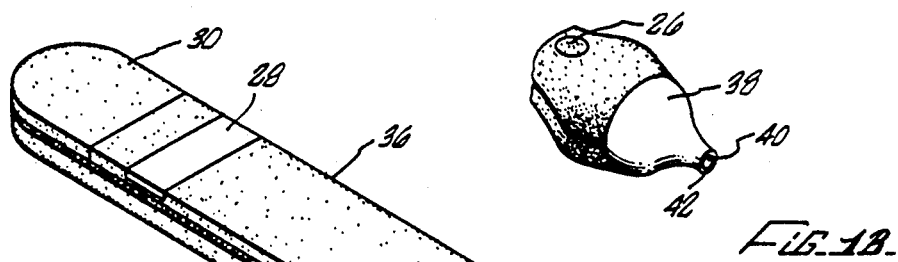
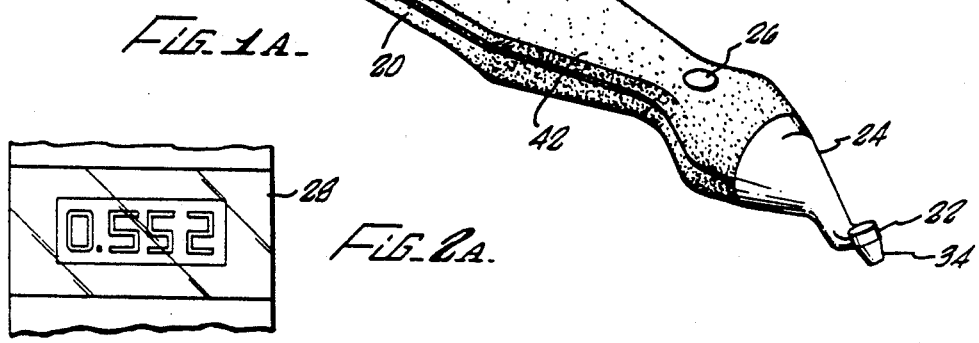
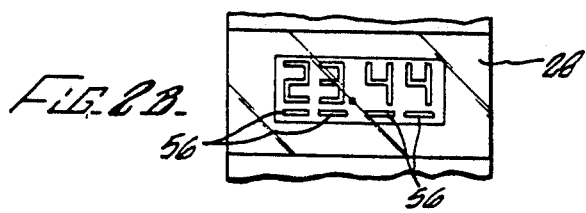
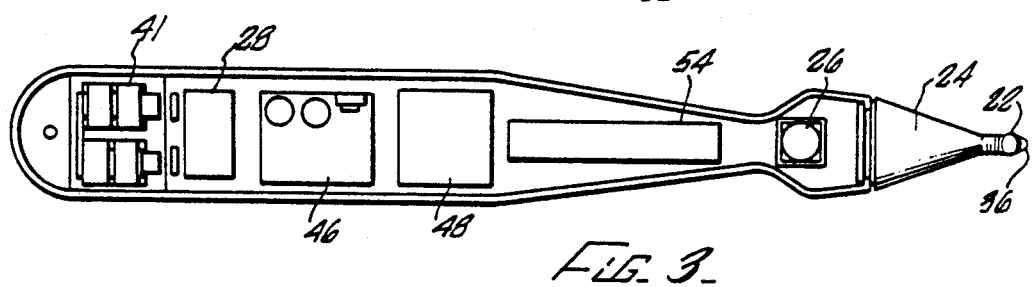
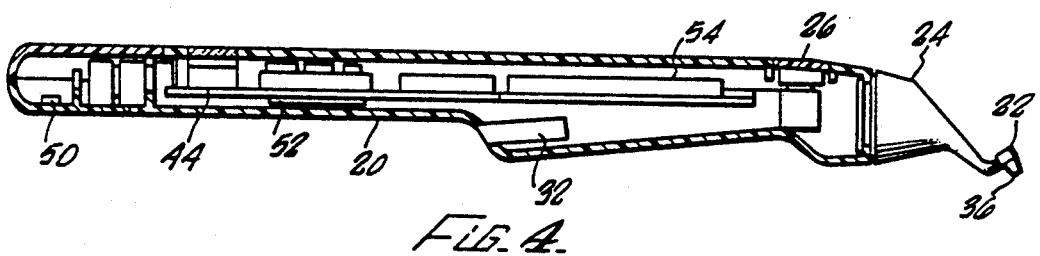

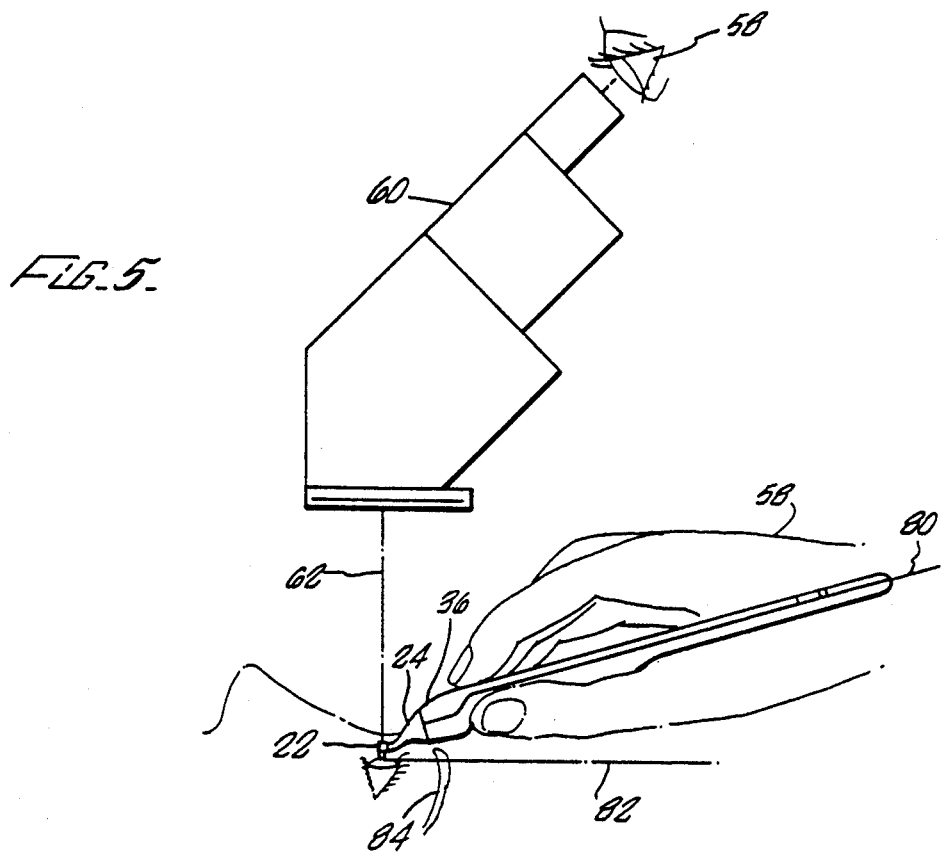
FIG._5.
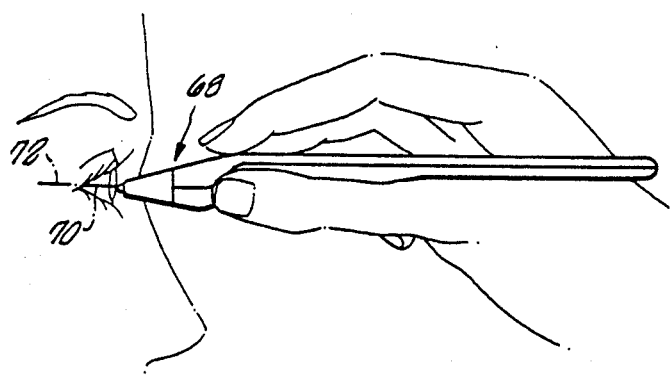
FIG._6.
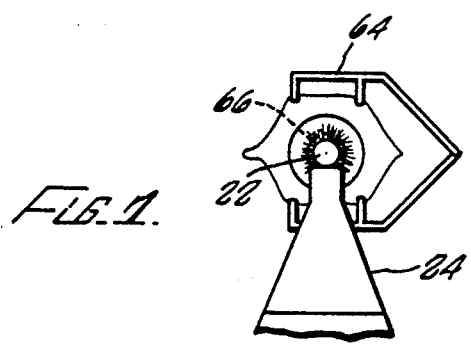
FIG._7.

SELF CONTAINED HAND HELD ULTRASONIC INSTRUMENT FOR OPHTHALMIC USE

This application is a continuation of application Ser. No. 352,681, filed May 10, 1989, now abandoned, which is a continuation of application Ser. No. 267,746, filed Nov. 2, 1988, now abandoned, which is a continuation of application Ser. No. 145,643, filed Jan. 13, 1988, now abandoned, which is a continuation of application Ser. No. 781,148, filed Sep. 23, 1985, now abandoned.

BACKGROUND OF THE INVENTION

Myopia (near-sightedness) is the most common optical refractive error. Over 133 million individuals in the United States wear some form of refractive correction, either in the form of spectacles or contact lenses.

Recently, surgical correction of refractive errors, or refractive surgery, has gained increasing popularity. The most popular form of refractive surgery is called radial keratotomy (RK). In this surgery, a series of radial incisions of precise depth are placed in the cornea, reflecting a change in its curvature and hence its refractive power. RK surgery was initially regarded with great skepticism by the ophthalmic community, however its effectiveness and relative safety have been demonstrated in the last few years. Accordingly, an increasing number of ophthamologists have been performing this operation.

The length and number of incisions required in an RK operation varies according to the degree of optical correction desired, and the depth of the incision is critical to the satisfactory outcome of the surgery. Inadequate depth will result in undercorrection, whereas excessive depth will result in overcorrection or perforation of the cornea and potentially serious harm to the eye. Accurate measurement of the corneal thickness is therefore essential to safe and successful RK surgery.

Instruments that measure corneal thickness are referred to as pachymeters. Early pachymeters were purely optical devices and had been shown to be imprecise. Ultrasonic technology is now routinely used to measure corneal thickness. All current instruments employ an ultrasonic probe which contacts the eye and which is connected via cable to a desk unit which is about the size of an oscilloscope. Some units have a smaller oscilloscope screen that displays the transducer tracings while other more recent units simply display a digital readout of the corneal thickness.

The most commonly performed operation in ophthalmology is cataract surgery. A cataract is an opacification of the biological lens inside the eye. In cataract extraction, one of the several techniques is used to remove the opacified lens material. Once removed, it is possible to implant an artificial lens in order to restore optical integrity to the eye, eliminating the need for thick cataract glasses or contact lenses.

When cataract surgery is performed, several measurements are necessary in order to calculate the precise power of the intraocular lens to be implanted. The important variables are corneal curvature (keratometry), size of the eye (axial length), knowledge of where inside the eye the inner ocular lens is to be implanted (interior or posterior chamber). Measurement of axial length is performed ultrasonically by a device referred to as a biometric ruler. Through such an instrument, the major internal structures of the eye can be imaged and their dimensions measured. Of importance in the measurement of true axial length is the distance from the cornea to the retina along the visual axis of the eye. The early biometric rulers employed a piezoelectric transducer, in a hand-held probe attached via a cable to an oscilloscope. It was necessary for the individual performing the examination to visually assess the oscilloscope signals and identify an axial scan. Second generation instruments still require the examiner to detect the pattern consistent with an axial scan. Then, electronics are used to calculate and display the desired measurement in millimeters. It would be desirable to have a self-contained, hand-held, digital, ultrasonic biometric ruler instrument for displaying the axial length of the eye using microprocessor technology to assess the echo waveforms and displaying digitally a readout representing as accurately as possible the true axial length of the eye.

CROSS REFERENCE TO RELATED APPLICATIONS

The present invention is related to the system and circuits disclosed in U.S. Pat. No. 4,817,432 entitled "Digital Ultrasonic Instrument for Ophthalmic Use" filed concurrently herewith in the names of David A. Wallace M.D., Steven E. Feldon M.D., Gary P. Mezack, Douglas L. Whiting Ph.D., William J. Dally and Scott A. Karns and the disclosure of which is incorporated herein by reference. The present invention is also related to the system disclosed in U.S. Pat. No. 4,747,296 entitled "Hand-Held Self-Contained Electronic Tonometer" filed concurrently herewith in the names of Steven E. Feldon M.D., David A. Wallace M.D., Robert A. Monsour and Gary P. Mezack and the disclosure of which is incorporated herein by reference.

SUMMARY OF THE INVENTION

The present invention relates to a completely portable, hand held digital ultrasonic instrument about the size and shape of an ordinary pen. The housing is contoured such that it can be easily grasped in the manner of a writing pen. An activation button is located on the interior dorsal surface in close approximation to the index fingertip of the user. A liquid crystal display provides a digital readout of the corneal thickness on the barrel of the instrument housing. The instrument incorporates a 10 MHz or 20 MHz solid phase piezoelectric transducer, a microprocessor, a gate array, a hybrid transceiver, a liquid crystal display, batteries and a removable battery cover. The pachymeter uses a 20 MHz transducer that is attached to a swan neck connector which is attached to the instrument housing. The biometric ruler uses a 10 MHz transducer that is attached to a truncated conical connector which is also attached to the instrument housing. In addition, a pinjack connector is available to link the unit to other electronic media such as a microcomputer, personal computer, or printer. When the 10 MHz transducer is used, the program in the microprocessor is changed to accommodate the different echo patterns that are measured when the axial length of the eye is measured as opposed to the corneal thickness.

BRIEF DESCRIPTION OF THE DRAWINGS

FIG. 1A is a perspective view of the instrument as a pachymeter with a 20 MHz transducer and FIG. 1B shows the biometric ruler with a 10 MHz transducer.

FIG. 2A shows a digital display for use with a 20 MHz transducer and FIG. 2B shows a digital display for use with a 10 MHz transducer.

FIG. 3 is a top view of the pachymeter with the top cover removed.

FIG. 4 is a side view of the pachymeter showing the various location of the component parts.

FIG. 5 is a perspective view of the pachymeter as it would be held by a user when the thickness of the cornea is measured.

FIG. 6 is a perspective view of the biometric ruler as it would be held by a user when the axial length of the eye is measured.

FIG. 7 shows a pachymeter with a 20 MHz transducer in contact with the eye as held open by a lid retractor.

DETAILED DESCRIPTION OF THE PREFERRED EMBODIMENT

Referring to FIG. 1A, the instrument comprises a housing 20 which is contoured such that it can be easily grasped, in the manner of a writing pen. The tip of the instrument is the piezoelectric ultrasonic transducer 22 mounted on a plastic standoff 34. The other functioning components of the instrument include an activation button 26, located on the anterior dorsal surface in close approximation to the index fingertip of the user, a liquid crystal display 28 (LCD), a reset button (not shown), a removable battery cover 30, and a pinjack connector 32 (FIG. 4).

The 20 MHz transducer 22 comprises a plastic, ultrasonically transparent, contact head 34, and a recessed piezoelectric ultrasonic transducer 22. This cone shaped contact head 34 is attached to the transducer 22 which is attached to the swan neck connector 24 which connects to the main housing 20 of the pachymeter 36. The backing of the transducer is a 0.005 inch piece of tungsten-loaded epoxy which is an acoustically inert material. The piezoelectric transducer element has a frequency of 20 MHz. It is activated by a hybrid transceiver which connects to a microprocessor a gate array. One to three pulses of current are delivered to the transducer from the hybrid transceiver. The first echo corresponds to the front corneal surface. The second echo corresponds to the back corneal surface. The time between the two corneal echoes is proportional to the corneal thickness. Because sound travels at a rate of approximately 1640 meters/sec through corneal tissue, the time between the emitted signal and the reflected echoes can be converted to millimeters, using standard formulae.

The active transducer element is opaque and is centered at the posterior edge of the cone shaped contact head 34. The contact head is made of a clear acrylic material that allows the instrument tip to be better visualized under the operating microscope 60 (FIG. 5). The small size of the transducer 22 and the contact head 34 minimizes the area of the corneal surface which is obscured by the transducer 22. In addition, the swan neck connector 24 is designed such that it is rather easy for the user to place the contact head 34 into contact with the corneal surface perpendicularly to the visual axis shown by dotted line 62 in FIG. 5. In essence, the combined clear acrylic contact head 34 and the swan neck connector 24 both facilitate perpendicular alignment of the transducer 22 to the corneal surface. The transducer must be aligned perpendicular to the corneal surface in order to obtain detectable echoes from the inner corneal surface adjacent to the aqueous humor. In addition, the shortest echographic distance corresponds to the actual corneal thickness. If the transducer 22 is slightly off perpendicular to the visual axis, then spurious readings may result.

To calibrate a pachymeter with a 20 MHz transducer, an acrylic multistepped calibration block, which simulates the corneal interfaces, is used which is placed on a flat surface. The pachymeter 36 is then held perpendicularly to the surface of the block and the activation switch 26 is pressed once and then released. A beeper and miniature speaker provide a series of clicks followed by a beep. The pachymeter reading from the surface will be displayed on the display 28. This output should be within 0.01 mm of the calibration block measurement printed on its surface.

When the instrument is used as a biometric ruler, the same housing 20 is used. The tip of the instrument is a piezoelectric ultrasonic transducer element (not shown) mounted within a standoff 38 as shown in FIG. 1B. A special acoustically mismatched damping material is utilized to prevent "ringing" of the ultrasonic transducer which might preclude interpretation or detection of early echoes. Other functional components of the instrument include an activation button 26 located on the anterior dorsal surface in the close approximation to the index fingertip of the user, liquid crystal display 28, a reset button (not shown), and a removable battery cover 30. The transducer head 42 is a focusing element with a focal length of 24 millimeters, corresponding to an area near the retina of the eye. The diameter of the focusing element is 0.3 inch. In the center of the focusing element is a light-emitting diode 40. The patient is asked to look at the light-emitting diode 40, which has been activated, as the probe is placed in contact with the corneal surface. This allows the patient to center the eye on the transducer, facilitating axial measurements.

The average speed of sound through the eye is approximately 1560 meters/second. The time between the emitted signal, corresponding to the corneal surface, and reflected echoes are then converted into millimeters using standard formulae. One to three pulses of current from the hybrid transceiver are delivered to activate the transducer. After sending out the ultrasonic signal, the transducer is used in a detection mode. The first echo corresponds to the transducer-corneal interface. All subsequent echoes are measured relative to this. The second echo, found within a "window" of 1.5 to 5 millimeters from the corneal surface, corresponds to the anterior lenticular surface. The third echo, falling into a window of 1.5 to 6.5 millimeters behind the anterior lenticular echo, corresponds to the posterior lenticular surface. The fourth echo, located 18.5 to 29.0 millimeters behind the corneal surface echo, corresponds to the retinal surface. The fifth echo, 0.29 to 2.5 millimeters behind the retina, corresponds to the scleral surface. Echoes which occur outside the given windows will be ignored. When the second echo through the fifth echo are detected simultaneously there is optimal alignment. The four annunciator bars 56, FIG. 2B, separately indicate the presence of these four echos.

The 10 MHz Transducer is calibrated by use of an acrylic block with multiple interfaces which simulates a standardized eye. This is placed on a flat surface and the transducer head 42 is then held perpendicular to the surface of the block and the activation switch 26 is pressed once and then released. A series of clicks will sound, following which there will be a beep. The biometric ruler reading from this source will be demonstrated on the display 28. This output should be within 0.1 millimeters of the calibration block measurement printed on its surface.

FIG. 2A shows typical information that is displayed on the digital readout 28 when the 20 MHz transducer is used and FIG. 2B shows typical information displayed when the 10 MHz transducer is substituted for the 20 MHz transducer of FIG. 1A.

FIG. 3 shows a top view of the instrument with the top cover 42 (FIG. 1A) removed. The batteries 41 are located to the rear of the instrument. The liquid crystal display 28 is connected to a circuit board 44 (FIG. 4) and is located adjacent to the microprocessor 46. A gate array 48 is located on the same circuit board 44 between the microprocessor 46 and the hybrid transceiver 54. The activation switch 26 is located between the hybrid transceiver 54 and the connector 24. The total length of the unit is approximately 7.25 inches and it weighs approximately 2 ounces.

FIG. 4 shows a sectional view of the housing 20 of the hand-held pachymeter 36 with the various components installed. The same housing 20 and component parts shown in FIG. 4 are used when the instrument is used as a biometric ruler except that the connector 38 and its associated parts are substituted for the connector 24 and its associated parts. At the rear end of the casing is located a reset switch 50 and a Murata beeper 52 is located directly beneath the microprocessor 46 on the opposite side of circuit board 44. There is a pinjack 32 located directly below the printed circuit board 44. This pinjack 32 is used to send data such as corneal thickness or axial length from the instrument, whether used as a pachymeter or biometric ruler, to outside instruments such as a microcomputer, a personal computer or printer.

All elements of the instrument are connected to a multilayered circuit board 44. Mounted off the circuit board are four silver oxide batteries 41. Mounted on the circuit board is the discrete circuitry related to transducer signal processing. Also on the circuit board are connectors to the display 28, the reset button 50, and the RS232 pinjack 32.

FIG. 5 shows the pachymeter 36 with a 20 MHz transducer 22 being used for measuring the thickness of the cornea. The user is able to look through a microscope 60 and at the same time grasp the pachymeter 36 in the manner shown in FIG. 5. The shape of the swan neck connector 24 allows the user 58 to position the transducer element 22 on the central axis of the cornea, shown by dotted line 62, and still be able to view the patient's eye through the microscope 60. Dotted line 82 shows the perpendicular tangent of the cornea to the visual axis shown by line 62. The central axis of the pachymeter 36, shown by dotted line 80, is approximately 27° from the tangent of the cornea shown by line 82. The swan neck connecter allows the pachymeter 36 to be comfortably held in a position in which the transducer 22 is aligned with the visual axis of the eye and the pachymeter clears the patient's eyebrow 84 and allows the user to comfortably rest his hand on the patient's forehead. A clearer view of what the user sees when viewing the transducer 22 in contact with the eye 65 is shown in FIG. 7. The lid retractor 64 holds the patient's eyelids in an open position to facilitate the thickness measurement. The size of the transducer 22 along with the swan neck connector 24 allows the user to partially view the optical zone as shown by dotted lines 66 in FIG. 7. The optical zone marks the central limit of the radial corneal cuts performed during radial keratotomy surgery. This zone, usually 3 to 4.5 millimeters in diameter, is demarcated by the surgeon by the superficial application of a calibrated trephine.

FIG. 6 shows a user holding the biometric ruler as it would be held when making an axial length measurement. The biometric ruler unit 68 is held perpendicular to the patient's eye 70 along the visual axis of the patient's eye shown by dotted line 72. The activation button 26, FIG. 1B, is depressed and the measurement sequence is initiated. The results of the successful measurement are displayed on the LCD 28 as shown in FIG. 2B.

In the case of aphakia, the anterior and posterior lenticular spikes are not available. Axial length calculation is required for the placement of secondary lens implants with appropriate power. Because it is impossible to align multiple interfaces to ensure axial scan, the reliability of such measurements is less than could be expected in aphakic patients. Therefore, in order to initiate an aphakia mode measurement, the activation button 26 is pressed twice in rapid succession. The patient is then asked to look at LED emitter 40 (FIG. 1B) in the middle of the focusing element 42 (FIG. 1B). Once the retinal and scleral spikes are identified using thresholding identification algorithms, the maximum length is sought in a manner analogous to the evaluation performed in the phakic examination. The results are displayed on the display 28, sent to the pinjack 32, and the annunciators 56, corresponding to the retinal and scleral spikes, are illuminated on the display 28. The biometric ruler 68 as shown in FIG. 6 weighs approximately 2 ounces and is approximately 7.25 inches in length.

When the activation switch has not been depressed for two minutes, the microprocessor 46 and transducer elements are automatically turned off in order to reduce power consumption and preserve the battery life. A small discrete circuit performs this function and also responds to depression of the activation button by activating the electronic elements and the transducer.

While the preferred embodiment of the system of the present invention has been illustrated and described, certain modifications and alternatives will be apparent to those skilled in the art and the present disclosure is intended to include such modifications and alternatives within the scope of the appended claims.

What is claimed is:

1. A self contained hand-held ultrasonic instrument for measuring ophthalmic thicknesses comprising a housing with an elongated body with a shape to enable said housing being grasped in the manner of a writing pen, said body having a central axis, a distal end, a top surface and said body having depressions toward the distal end to facilitate grasping said instrument in the manner of a writing pen;

a swan neck connector having a conically tapering neck that is angled downward to a first area connected to a transducer, a second area of said connector being connected to the distal end of said housing and the central axis of said transducer being disposed at such an angle off the central axis of said elongated body that said instrument can be comfortably held in a position in which said elongated body does not contact a patient's eyebrow and in which a user can rest said user's hand on said patient's forehead and in which said transducer is aligned with the visual axis of one of said patient's eyes, the size and disposition of said transducer arranged to permit said user to partially view an optical zone of said one of patient's eyes, and a digital display located on the top surface of said body and said body housing an interconnected power supply, a gate array connected to a microprocessor and transmitter/receiver, and said microprocessor is connected to said digital display and said transmitter/receiver.

2. The instrument of claim 1,
wherein said transducer comprises a piezoelectric ultrasonic transducer centered at the posterior edge of a clear cone shaped contact head.

3. A self contained hand-held ultrasonic instrument for measuring axial length of an eye comprising:
a writing pen shaped housing having a central axis, a distal end, a top surface and depressions toward the distal end to facilitate grasping in the manner of a writing pen;
a truncated conical section connected to the distal end of said housing, narrowing distally along the central axis and said section containing a transducer; and
said housing further containing interconnected circuitry including a digital display located on the top surface of said housing, a power supply, a gate array, a transmitter/receiver, and a microprocessor.

4. The instrument of claim 3,
wherein said conical section also contains a focusing element and a light source disposed within the focussing element so that a patient can center the patient's eye on said transducer by looking at said light source.

5. The instrument of claim 3,
wherein said microprocessor comprises a memory having stored therein a program to ignore an ultrasonic echo from a signal sent by said transducer unless said echo is detected by said transducer corresponding to an expected window.

6. The instrument of claim 5,
wherein said window is a period of time corresponding to any one of the following approximate distance ranges: 1.5 to 5 mm. behind the corneal surface, corresponding to the anterior lenticular surface; 1.5 to 6.5 mm. behind the anterior lenticular surface, corresponding to the posterior lenticular surface; 18.5 to 29.0 mm. behind the corneal surface, corresponding to the retinal surface; and 0.29 to 2.5 mm. behind the retina, corresponding to the scleral surface.

7. A self contained hand-held ultrasonic pachymeter comprising:
a housing with an elongated body with a shape to enable said housing being grasped in the manner of a writing pen, said body having a central axis, a distal end, a top surface and said body having depressions toward the distal end to facilitate grasping said instrument in the manner of a writing pen;
a swan neck connector having a conically tapering neck that is angled downward to a first area connected to a 20 MHz piezoelectric transducer centered at the posterior edge of a clear cone shaped contact head, a second area of said connector being connected to the distal end of said housing and the central axis of said transducer being disposed at such an angle off the central axis of said elongated body, that said instrument can be comfortably held in a position in which said elongated body does not contact a patient's eyebrow and in which a user can rest said user's hand on said patient's forehead and in which said transducer is aligned with the visual axis of one of said patient's eyes, the size and disposition of said transducer arranged to permit said user to partially view an optical zone of said one of patient's eyes, and
a digital display located on the top surface of said body and said body housing logic means for assessing echo waveforms and connected to a miniature speaker, to an external pinjack, to an activation button, and to said digital display.

8. A self-contained hand-held ultrasonic biometric ruler comprising:
a housing with an elongated body with a shape to enable said housing being grasped in the manner of a writing pen, said body having a central axis, a distal end, a top surface and said body having depressions toward the distal end to facilitate grasping said instrument in the manner of a writing pen;
a truncated conical section connected to the distal end of said housing, narrowing distally along the central axis of the elongated body, and said section containing a 10 MHz transducer, a focusing element, and a light-emitting diode disposed within the focussing element so that a patient centers his eye on said transducer when the patient looks at said diode, said body housing a power supply interconnected logical means, for assessing echo waveforms, digital display means for displaying a readout representing a measurement of the corneal thickness or axial length of an eye, an external pinjack for optional transmission of biometric information, a miniature speaker, and an activation button.

9. A system for measuring ophthalmic thickness comprising:
a miniaturized housing having an integral, self-contained power supply, an elongated body having calculating and displaying means for calculating and displaying corneal thickness and axial length of an eye, a central axis, a distal end, and depressions toward the distal end to facilitate grasping said housing in the manner of a writing pen;
a first connector, in the shape of a swan neck, said connector having a conically tapered neck that is angled downward to a first area connected to a first piezoelectric transducer which is centered at the posterior edge of a clear cone shaped contact head, a second area of said connector being connectable to the distal end of said housing and the central axis of said transducer being disposed at an angle approximately 63% off the central axis of said elongated body; and
a second connector, in the shape of a truncated cone, said connector narrowing distally along the central axis of said elongated body and comprising a second transducer;
means for attaching the connectors to the housing whereby attachment of the first connector to said housing couples said first transducer to said calculating and displaying means to provide first measurement means for reading corneal thickness of the eye and attachment of the second connector to said housing couples said second transducer to said calculating and displaying means to provide second measurement means for reading the axial length of the eye.

* * * * *

UNITED STATES PATENT AND TRADEMARK OFFICE
CERTIFICATE OF CORRECTION

PATENT NO. : 5,165,415

DATED : Nov. 24, 1992

INVENTOR(S) : David A. Wallace, Steven E. Feldon

It is certified that error appears in the above-identified patent and that said Letters Patent is hereby corrected as shown below:

Column 3, line 41, after "microprocessor" add --and--.

Signed and Sealed this

Sixth Day of July, 1993

Attest:

MICHAEL K. KIRK

Attesting Officer

Acting Commissioner of Patents and Trademarks